United States Patent [19]
Takahashi

[11] Patent Number: 5,995,859
[45] Date of Patent: Nov. 30, 1999

[54] METHOD AND APPARATUS FOR ACCURATELY MEASURING THE SATURATED OXYGEN IN ARTERIAL BLOOD BY SUBSTANTIALLY ELIMINATING NOISE FROM THE MEASUREMENT SIGNAL

[75] Inventor: Iwao Takahashi, Tokyo, Japan

[73] Assignee: Nihon Kohden Corporation, Tokyo, Japan

[21] Appl. No.: 08/979,859

[22] Filed: Nov. 26, 1997

Related U.S. Application Data

[63] Continuation-in-part of application No. 08/388,427, Feb. 14, 1995, abandoned.

[30] Foreign Application Priority Data

Feb. 14, 1994 [JP] Japan .................................. 6-017340

[51] Int. Cl.[6] .................................................. A61B 5/00
[52] U.S. Cl. ............................................. 600/323; 600/336
[58] Field of Search ..................................... 600/310, 314, 600/315, 316, 322, 323, 336, 473, 476; 356/39–41

[56] References Cited

U.S. PATENT DOCUMENTS

| | | | |
|---|---|---|---|
| 4,621,643 | 11/1986 | New, Jr., et al. ........................ | 128/633 |
| 4,863,265 | 9/1989 | Flower et al. ........................... | 128/633 |
| 5,253,646 | 10/1993 | Delpy et al. ............................. | 128/633 |
| 5,282,466 | 2/1994 | Duffy et al. ............................. | 128/633 |
| 5,632,272 | 5/1997 | Diab et al. ............................... | 600/323 |

*Primary Examiner*—Lee Cohen
*Assistant Examiner*—Bryan K. Yarnell
*Attorney, Agent, or Firm*—Sughrue, Mion, Zinn, Macpeak & Seas, PLLC

[57] ABSTRACT

A pulse oximeter includes a light-emitting device for repeating red light emission, infrared light emission, and no light emission with respect to an object to be measured every data sampling cycle in a measurement of a saturated oxygen in arterial blood, a light-receiving device for outputting a light-receiving signal obtained by receiving transmitted light or reflected light from the object to be measured; a noise level detecting device for detecting from the light-receiving signal a noise signal level at the time of no light emission in the light-receiving device, and a light-receiving signal generating device for obtaining a light-receiving signal of a level corresponding only to the red light emission and the infrared light emission by subtracting the noise signal level from each of light-receiving signal levels of the red light emission and the infrared light emission.

23 Claims, 9 Drawing Sheets

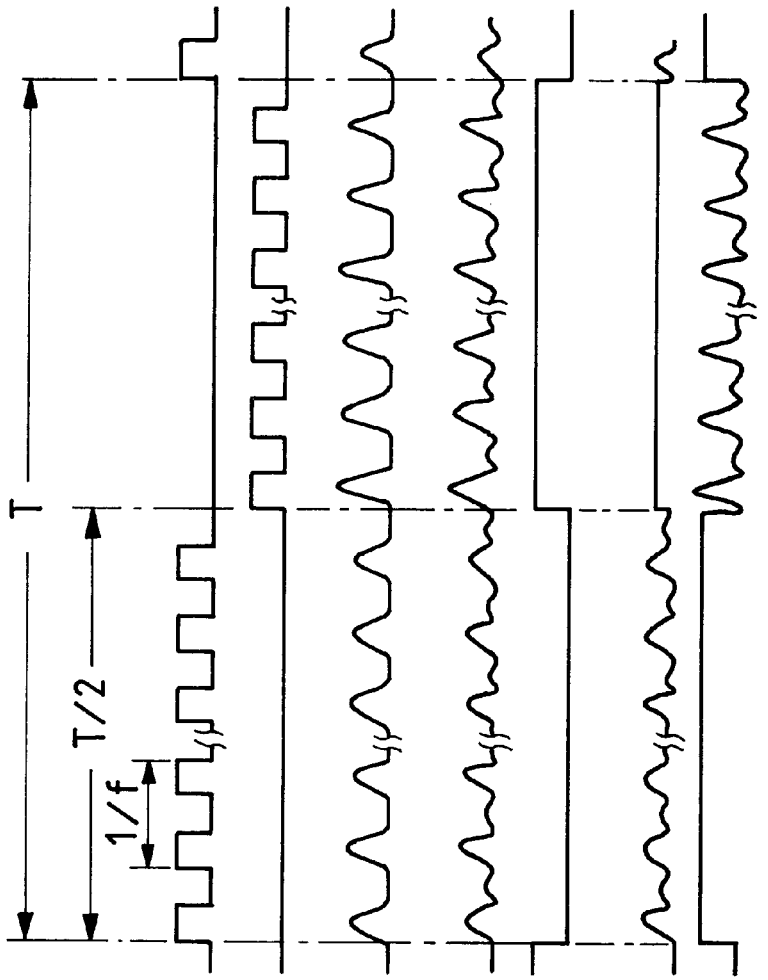

METHOD AND APPARATUS FOR ACCURATELY MEASURING THE SATURATED OXYGEN IN ARTERIAL BLOOD BY SUBSTANTIALLY ELIMINATING NOISE FROM THE MEASUREMENT SIGNAL

This is a Continuation of application Ser. No. 08/388,427 filed Feb. 14, 1995, now abandoned.

BACKGROUND OF THE INVENTION

1. Field of the Invention

The invention relates to a pulse oximeter that not only detects an external noise level affecting measurement of the saturated oxygen in the arterial blood ($SPO_2$) so that a measurement with the external noise eliminated can be obtained, but also displays an alarm in the case where an accurate measurement cannot be made.

2. Related Art

In the conventional $SPO_2$ measurement, it is known that the light-receiving element of a measuring probe is affected not only by external light from light sources other than infrared light and red light used in the measurement, e.g., a fluorescent light and the like, but also by induced noise from external devices, e.g., an electric blanket and the like. To overcome this problem, various methods have been proposed, the methods being intended to suppress disturbance affecting a target signal and thereby obtain only the target signal.

FIG. 8 is a block diagram showing a configuration of such a conventional pulse oximeter with part of circuits thereof. In FIG. 8, this conventional example is provided as including light-emitting diodes 2a and 2b and a control circuit 3. The light-emitting diode 2a blinks red (R) light at a frequency f during a first half interval, which is a data sampling cycle T/2, by causing a switching transistor to be turned on and off by a R light emission drive signal. The light-emitting diode 2b blinks infrared (IR) light at the frequency f during the latter half interval, which is a data sampling cycle T/2, by causing a switching transistor to be turned on and off by an IR light emission drive signal. The control circuit 3 controls the emissions so that emission of the R light and the IR light from the light-emitting diodes 2a, 2b is repeated alternately at the frequency f. The control circuit 3 has a CPU, a ROM that stores a control program, a working RAM, and the like.

This conventional example is further provided as having a light-receiving diode 4, a current/voltage converting and amplifying circuit 5, a bandpass filter (BPF) 6, and an AM detecting circuit 7. The light-receiving diode 4 receives transmitted light or reflected light obtained at the time the R light and the IR light from the light-emitting diodes 2a, 2b are irradiated onto the arterial blood, and outputs a photoelectrically converted light-receiving signal. The current/voltage converting and amplifying circuit 5 outputs an amplified light-receiving signal obtained by converting the photoelectrically converted current from the light-receiving diode 4 to a voltage and amplifying the converted voltage. The BPF 6 cuts off low and high frequency ranges of the light-receiving signal from the current/voltage converting and amplifying circuit 5 by a center frequency f. The AM detecting circuit 7 has operational amplifiers and diodes, and outputs a detection signal by detecting (rectifying both waves) the light-receiving signal from the BPF 6.

This conventional example is still further provided as including a switching circuit 8, an integrating circuit 9, and a radio transmission section 10. The switching circuit 8 performs a switching operation in response to an R/IR switching signal from the control circuit 3, the switching operation being such that a light-receiving signal of the reflected light of each of the R light and the IR light can be introduced in the order of irradiation of the R light and the IR light while dividing a single data sampling time (cycle T) into two intervals. The integrating circuit 9 alternately outputs an R signal and an IR signal, each being obtained by integrating the detection signal output from the switching circuit 8 by a constant determined by a capacitor C and a resistor R, based on the R/IR switching signal. The radio transmission section 10 transmits measured data from the control circuit 3.

An operation of this conventional example will be described next.

FIGS. 9(a) to (g) are timing charts showing processed waveforms and the processing timings in the operation of this conventional example. In FIGS. 8 and 9, the R light and the IR light are emitted alternately with the R/IR light emission drive signals shown in FIGS. 9(a) and (b) supplied every cycle T/2 to the light-emitting diodes 2a, 2b through transistors Q1, Q2 from the control circuit 3. The light-receiving diode 4 receives transmitted light or reflected light obtained at the time these emitted lights are irradiated onto the arterial blood, and outputs a photoelectrically converted light-receiving signal. This light-receiving signal is converted to a voltage and the converted voltage is amplified to obtain an amplified light-receiving signal shown in FIG. 9(c) by the current/voltage converting and amplifying circuit 5. Such amplified light-receiving signal is then output to the BPF 6. The BPF 6 passes the amplified light-receiving signal only through a pass band whose center frequency is f.

The amplified light-receiving signal from the BPF 6 is detected by the AM detecting circuit 7. A detection signal shown in FIG. 9(d) is output to a movable contact c of the switching circuit 8. The movable contact c is switched at a cycle of T/2 of the R/IR switching signal shown in FIG. 9(e) from the control circuit 3, and allows the detection signal to be supplied to the integrating circuit 9 through fixed contacts a, b in such a manner as to correspond to the light emission cycles of the R light and the IR light. It is from the integrating circuit 9 that outputs an R signal and an IR signal shown in FIGS. 9(f), (g) obtained by integrating the detection signal by the CR constant. The level of the R signal or the IR signal is equal to the transmitted light or reflected light of the R light and the IR light irradiated onto the arterial blood. That is, such level is equal to an $SPO_2$ measurement.

In this case, if the light-emitting frequency f of the light-emitting diodes 2a, 2b is increased compared with a conventional frequency so that an amplified light-receiving signal is allowed to pass only the pass band of the BPF 6 (whose center frequency is f), then the pass band can be narrowed to cut off noise in both low and high frequency ranges. That is, many external noises disturbing $SPO_2$ measurement are distributed in relatively low frequencies that are only several times the ordinary commercial ac power frequency, and these external noises are eliminated by the BPF 6 to thereby improve discrimination of the target signal components (R light and IR light), which therefore allows accurate measurement to be made.

However, while the aforementioned conventional pulse oximeter not only emits the R light and the IR light at a higher light-emitting frequency f than the conventional frequency, but also passes the amplified light-receiving signal only through the pass band (whose center frequency is f) of the BPF 6 to allow discrimination of the external noise from the signal components to be improved, such method is not effective with respect to a diversity of external noises, and in the case where a frequency component close to the light-emitting frequency f is present in a noise, i.e., in the case where the so-called "disturbance" is present, accurate measurement cannot be made.

That is, the frequency component of the external noise close to the light-emitting frequency f is superimposed on the detection signal, which in turn adds an offset voltage to the R signal and the IR signal from the integrating circuit 9. In addition, beat sound due to a phase difference between the frequency f and the light-emitting cycle T is produced as a noise signal.

Under these circumstances, the conventional pulse oximeter displays $SPO_2$ measurements on a display screen without eliminating the noise. In other words, since the operator cannot identify inaccurate measurements with noise superimposed thereon, no such measures to obtain accurate measurements as changing the measurement site and turning off the power of the noise source can be taken, which has been a shortcoming encountered by the conventional example.

SUMMARY OF THE INVENTION

The invention has been made to overcome such problems addressed by the conventional art. Accordingly, the object of the invention is to provide a pulse oximeter that not only allows accurate measurement with external noise signal levels affecting quantitatively detected $SPO_2$ measurement substantially eliminated, but also allows accurate measurement to be made even in the case where the external noise cannot be eliminated by alarming an operator to that effect and thereby allowing the operator to make accurate measurement based on such alarm.

According to an aspect of the present invention, there is provided a pulse oximeter that includes: a light-emitting means for repeating red light emission, infrared light emission, and no light emission with respect to an object to be measured every data sampling cycle in a measurement of a saturated oxygen in arterial blood; a light-receiving means for outputting a light-receiving signal obtained by receiving transmitted light or reflected light from the object to be measured; a noise level detecting means for detecting from the light-receiving signal a noise signal level at the time of no light emission in the light-receiving means; and a light-receiving signal generating means for obtaining a light-receiving signal of a level corresponding only to the red light emission and the infrared light emission by subtracting the noise signal level from each of light-receiving signal levels of the red light emission and the infrared light emission.

According to another aspect of the present invention, there is provided a pulse oximeter that includes: a storage means for storing light-receiving signal levels corresponding to the red light emission, the infrared light emission, and the no light emission as well as noise signal levels corresponding to the no light emission in a plurality of data sampling cycles repeated by the light-emitting means; and a judging means for judging whether a noise level in the plurality of data sampling cycles in data stored in the storage means is approximate or not; and in such pulse oximeter, when the judging means judges that the noise signal levels are approximate, the light-receiving signal generating means outputs a light-receiving signal of a level corresponding only to the red light emission and the infrared light emission obtained by subtracting the noise signal level from each of light-receiving signal levels of the red light emission and the infrared light emission.

According to another aspect of the present invention, there is provided a pulse oximeter that includes: light-receiving means including an integrating circuit for outputting a signal obtained by integrating a detection signal for each of the red light emission, the infrared light emission, and the no light emission, the detection signal being a signal obtained by detecting the light-receiving signal from a light-receiving element having received the transmitted light or reflected light from the object to be measured; and a level of the integrated light-receiving signal corresponding to the red light emission, the infrared light emission, and the no light emission is stored by the storage means.

According to another aspect of the present invention, there is provided a pulse oximeter that includes: a display means for giving an indication that an external noise level cannot be eliminated by means of an on-screen display, a sound output, a synthetic voice output, a light emission either singly or in combination when the judging means judges that the noise signal levels in the plurality of data sampling cycles among the data stored in the storage means are not approximate.

According to another aspect of the present invention, a pulse oximeter of the present invention eliminates noise caused by surrounding light by sequentially driving a light source to emit red light, infrared light, and no light and subtracting a no light detection signal as the noise caused by surrounding light from respective red, infrared, and no light detection signals, provided in that time-dependent change in a no light signal level (a surrounding light noise level) is monitored, and that an alarm is given when a noise that cannot be eliminated by the aforementioned method such as a pulsating noise and beat is judged to be present, so that an operator is informed that accurate saturated oxygen measurement cannot be made.

The pulse oximeter detects a noise signal level at the time of no light emission from a light-receiving signal of the transmitted light or reflected light obtained when light emission in the red light emission interval, the infrared light emission interval, and the no light emission interval is repeated with respect to the object to be measured every data sampling cycle, and obtains only a light-receiving signal level corresponding to the transmitted light or reflected light obtained by subtracting the noise signal level from the light-receiving signal level. Therefore, accurate measurements can be obtained.

The pulse oximeter stores light-receiving signal levels corresponding to the red light emission, infrared light emission, and no light emission intervals as well as noise signal levels corresponding to the no light emission interval in a plurality of data sampling cycles, and outputs a signal level obtained by subtracting a noise signal level from each of light-receiving signal levels at the time of the red light emission and the infrared light emission when the noise signal levels in the stored data in the plurality of data sampling cycles are approximate. Therefore, accurate measurements can be obtained.

The pulse oximeter of the present invention given an indication that an external noise level cannot be eliminated by means of an on-screen display, a sound output, a synthetic voice output, a light emission either singly or in combination when the judging means judges that the noise signal levels in the plurality of data sampling cycles among the data stored in the storage means are not approximate. Therefore, if the external noise affects accurate measurement, the pulse oximeter alarms the operator by displaying such condition. As a result of this operation, the operator can take such effective measures as stopping the measurement at a site full of disturbance and turning off the power sources of noise generating devices at another site or at the same site so that accurate measurement can be made thereafter.

BRIEF DESCRIPTION OF THE DRAWINGS

FIGS. 9(a) to (g) are timing charts showing the waveforms of processed signals and the processing timings in the conventional example.

DETAILED DESCRIPTION OF THE PREFERRED EMBODIMENTS

Figure 1:
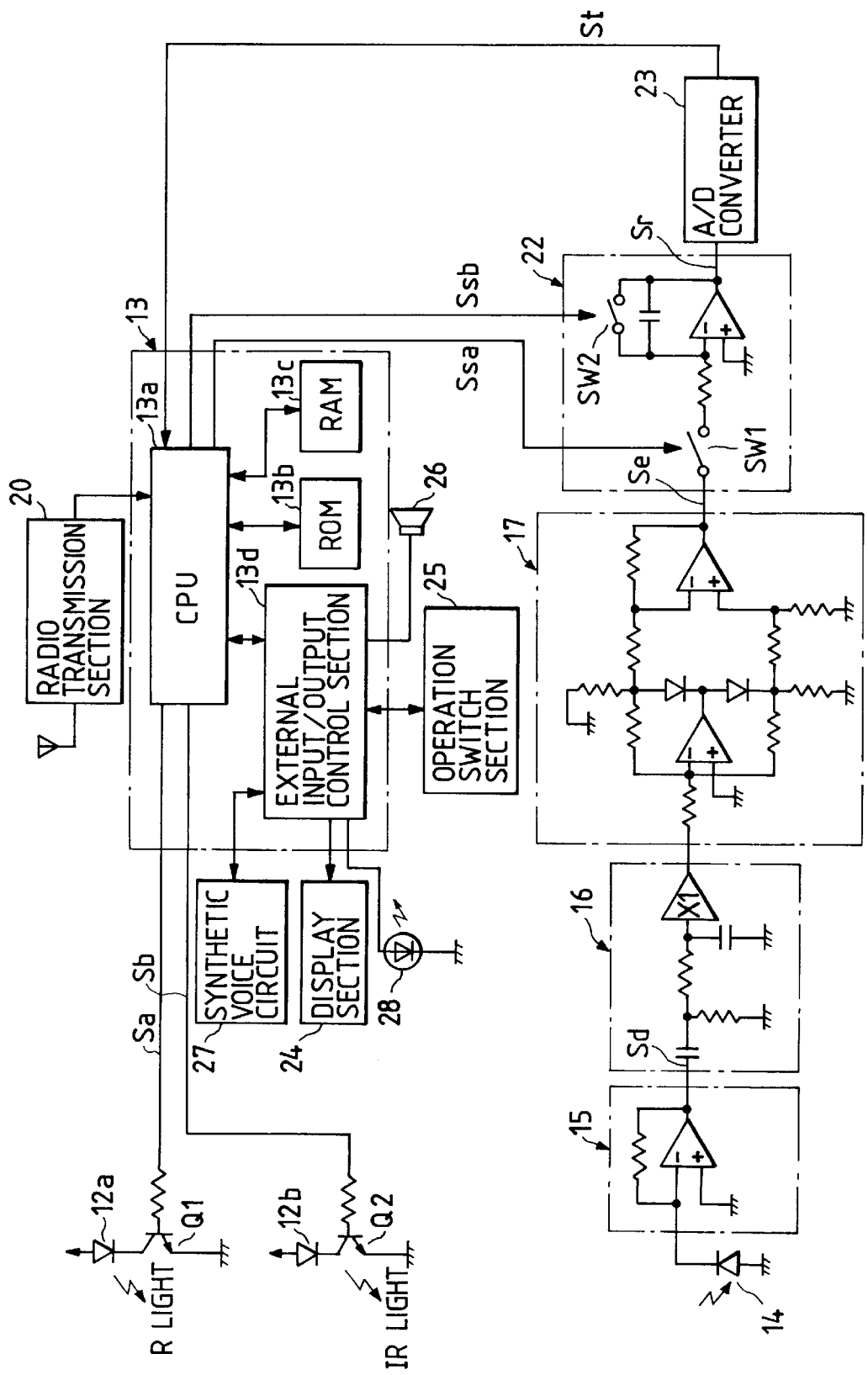
FIG. 1 is a block diagram showing a configuration of a pulse oximeter, which is a first embodiment of the invention, with part of circuits thereof.

Pulse oximeters, which are embodiments of the invention, will now be described in detail with reference to the drawings. FIG. 1 is a block diagram showing a configuration of a first embodiment of the invention with part of circuits thereof. The embodiment shown in FIG. 1 includes a light-emitting diode 12a and a light-emitting diode 12b. The light-emitting diode 12a emits red (R) light by causing a switching transistor Q1 to be turned on and off by an R light emission drive signal Sa whose frequency is f in a first interval, which is one of three intervals into which a single data sampling time (cycle T) is divided. The light-emitting diode 12b emits infrared (IR) light by causing a switching transistor Q2 to be turned on and off by an IR light emission drive signal Sb whose frequency is f in a second interval, which is another one of the three intervals into which the single data sampling time (cycle T) is divided.

Further, as will be described in detail later, a control circuit 13 is arranged in the first embodiment. The control circuit 13 measures the oxygen saturation in the arterial blood (SPO$_2$) by controlling the emission of R light in the first interval, the emission of IR light in the second 112 interval, and the darkness with no emission of light in the third interval, which are the three intervals into which the single data sampling time (cycle T) is divided. The control circuit 13 has a CPU 13a, a ROM 13b that stores a control program of the pulse oximeter, a working RAM 13c, and an external input/output (I/O) control section 13d.

Also in this embodiment are a light-receiving diode 14 and a current/voltage converting and amplifying circuit 15.

The light-receiving diode 14, connected to the control circuit 13, outputs a light-receiving signal obtained by receiving transmitted light or reflected light when the R light and the IR light from the light-emitting diodes 12a, 12b are irradiated onto the arterial blood and photoelectrically converts such received light. The current/voltage converting and amplifying circuit 15, involving an operational amplifier, converts photoelectrically converted current from the light-receiving diode 14 into a voltage, and outputs an amplified light-receiving signal Sd.

Still further, in this embodiment are a bandpass filter (BPF) 16, an AM detecting circuit 17, and an integrator 22. The BPF 16 outputs a light-receiving signal obtained by cutting off the lower frequency range of the amplified light-receiving signal Sd from the current/voltage converting and amplifying circuit 15, and includes resistors, capacitors, and an operational amplifier (buffer). The BPF 16 has a pass band whose center frequency is f. The AM detector 17 has operational amplifiers and diodes, and outputs a detection signal Se obtained by detecting (rectifying both waves) the light-receiving signal from the BPF 16. The integrator 22 outputs an integrated signal Sr obtained by integrating the detection signal Se based on control signals Ssa, Ssb from the control circuit 13. This integrator 22 has a switch SW1 that intermittently applies the detection signal Se, a switch SW2 that charges and discharges a capacitor C by opening and closing both terminals of the capacitor C, as well as a resistor R, the capacitor C, and an operational amplifier for obtaining an integrated value.

Still further, in this embodiment are an A/D converter 23, a display section 24, an operation switch section 25, a loudspeaker 26, a synthetic voice circuit 27, and a light-emitting diode 28. The A/D converter 23 converts the integrated signal Sr from the integrator 22 into a digital signal, and outputs the digital signal to the control circuit 13. The display section 24 displays detection of an external noise level affecting accurate SPO$_2$ measurement upon detection of such external noise level. The operation switch section 25 not only sets a threshold for detecting such external noise level affecting accurate SPO$_2$ measurement, but also specifies an alarm display mode when such external noise level is detected. The loudspeaker 26 that outputs an alarm sound upon detection of the external noise level affecting accurate SPO$_2$ measurement. The synthetic voice circuit 27 outputs an alarm message in the form of a synthetic voice. The light-emitting diode 28 displays the alarm message by blinking.

An operation of the first embodiment will be described next.

Figure 2:
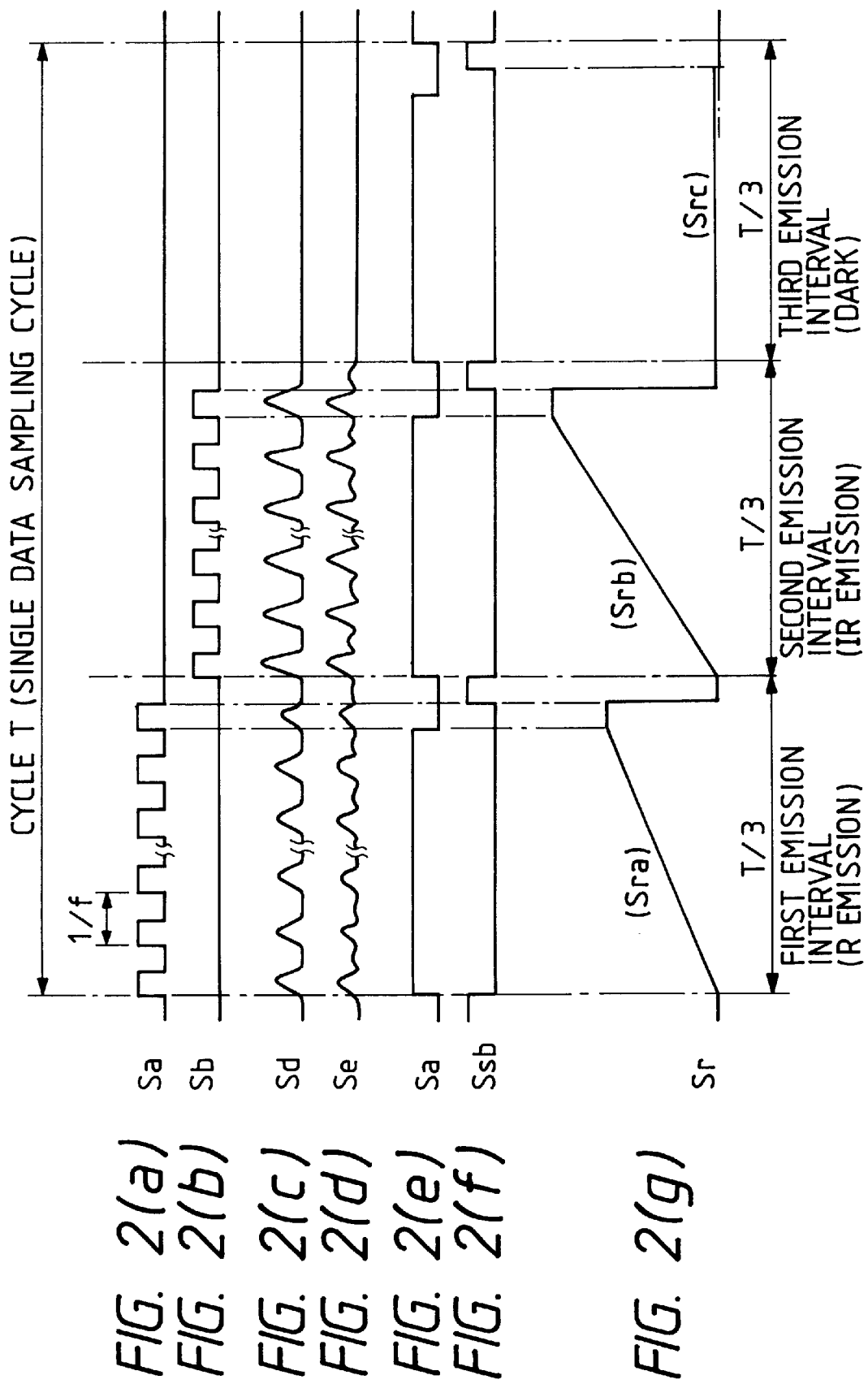
FIGS. 2(a) to (g) are timing charts showing the waveforms of signals processed at respective circuits and the processing timings in an operation of the first embodiment.

FIG. 2 is a diagram showing the waveforms of signals processed at respective circuits in the basic operation of the first embodiment. In FIG. 2, the operation is controlled such that the respective intervals, the first R light emission interval, the second IR light emission interval, and the third dark interval, into which a single data sampling time (cycle T) is divided, are repeated.

The control circuit 13 reads the control program of this pulse oximeter from the ROM 13b to start the control. First, the R light emission drive signal Sa and the IR light emission drive signal Sb shown in FIGS. 2(a) and (b) are supplied to the light-emitting diodes 12a, 12b via the transistors in the first interval and the successive second interval, each interval having a cycle of T/3, and these intervals are followed by the dark interval during which the sending of the R light emission drive signal Sa and the IR light emission drive signal Sb is interrupted. This cycle having three intervals is repeated. Then, the transmitted light or reflected light obtained at the time the R light and the IR light are irradiated onto the arterial blood of a subject is received by the light-receiving diode 14. The photoelectrically converted current of the received light is converted into a voltage and the converted voltage is amplified by the current/voltage converting and amplifying circuit 15. The amplified light-receiving signal Sd shown in FIG. 2(c) is output to the BPF 16. The BPF 16 passes only a component of this amplified light-receiving signal Sd, the component matching the pass band whose center frequency is f. That is, noise signals present in both low and high ranges of the frequency f are eliminated.

The amplified light-receiving signal Sd from the BPF 16 is detected by the AM detecting circuit 17, and the detection signal Se shown in FIG. 2(d) is output to the integrator 22. The integrator 22 turns the switch SW1 on upon rise of each of the first to third intervals of the data sampling time (cycle T) and off before the rise of a next interval by the control signal Ssa shown in FIG. 2(e). The switch SW2 is turned on after the switch SW1 has been turned off and before the next interval rises. That is, the capacitor C is short-circuited to discharge and start integration of the next interval. As a result of this operation, an integrated signal Sr shown in FIG. 2(g) is obtained. The integrated signal Sr has an R signal Sra, an IR signal Srb, and a dark signal Src in succession, the signals Sra, Srb, and Src corresponding to the R light emission in the first interval, the IR light emission in the second interval, and the darkness in the third interval, into which intervals the cycle T is divided.

The voltages of the R signal Sra and the IR signal Srb are converted into digital values by the A/D converter 23. This digital integrated signal St is applied to the control circuit 13, and the control circuit 13 then eliminates noise through the external I/O control section 13d and thereby produces an R signal Sra and an IR signal Srb that are only light-receiving signals corresponding to the light emissions, as will be described in more detail later. In addition, if the noise cannot be eliminated, the control circuit 13 gives a message indicating such condition to the operator. The processed data is not only displayed on the display section 24 but also sent to a data gathering apparatus, e.g., a host computer, installed in a remote site through a radio transmission section 20 and an antenna.

An operation of the pulse oximeter in the case where noise close to the frequency f is generated will be described next.

Figure 3:
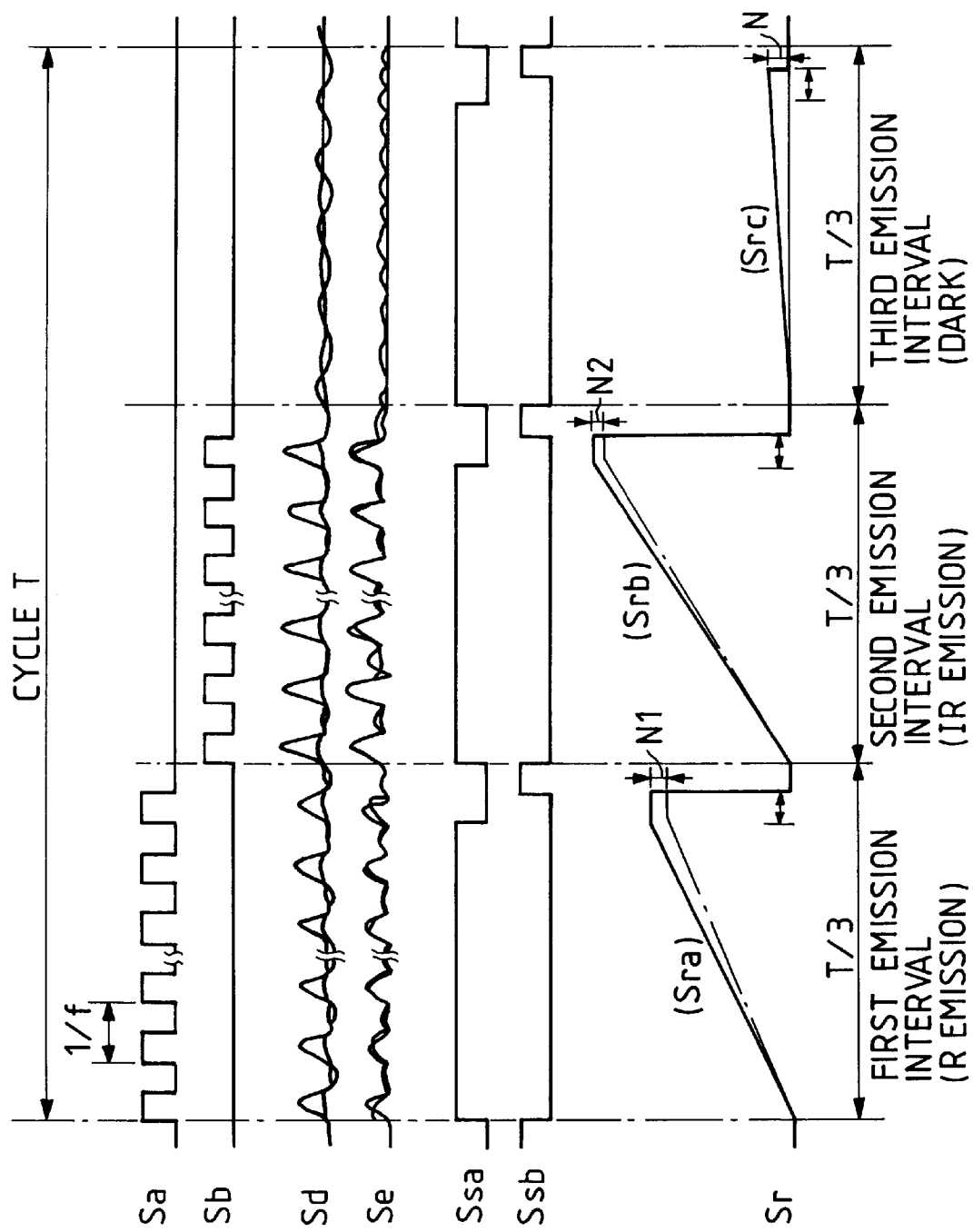
FIGS. 3(a) to (g) are timing charts showing the waveforms of signals processed at respective circuits and the processing timings in the case where noise is present in the operation of the first embodiment.
Figure 4:
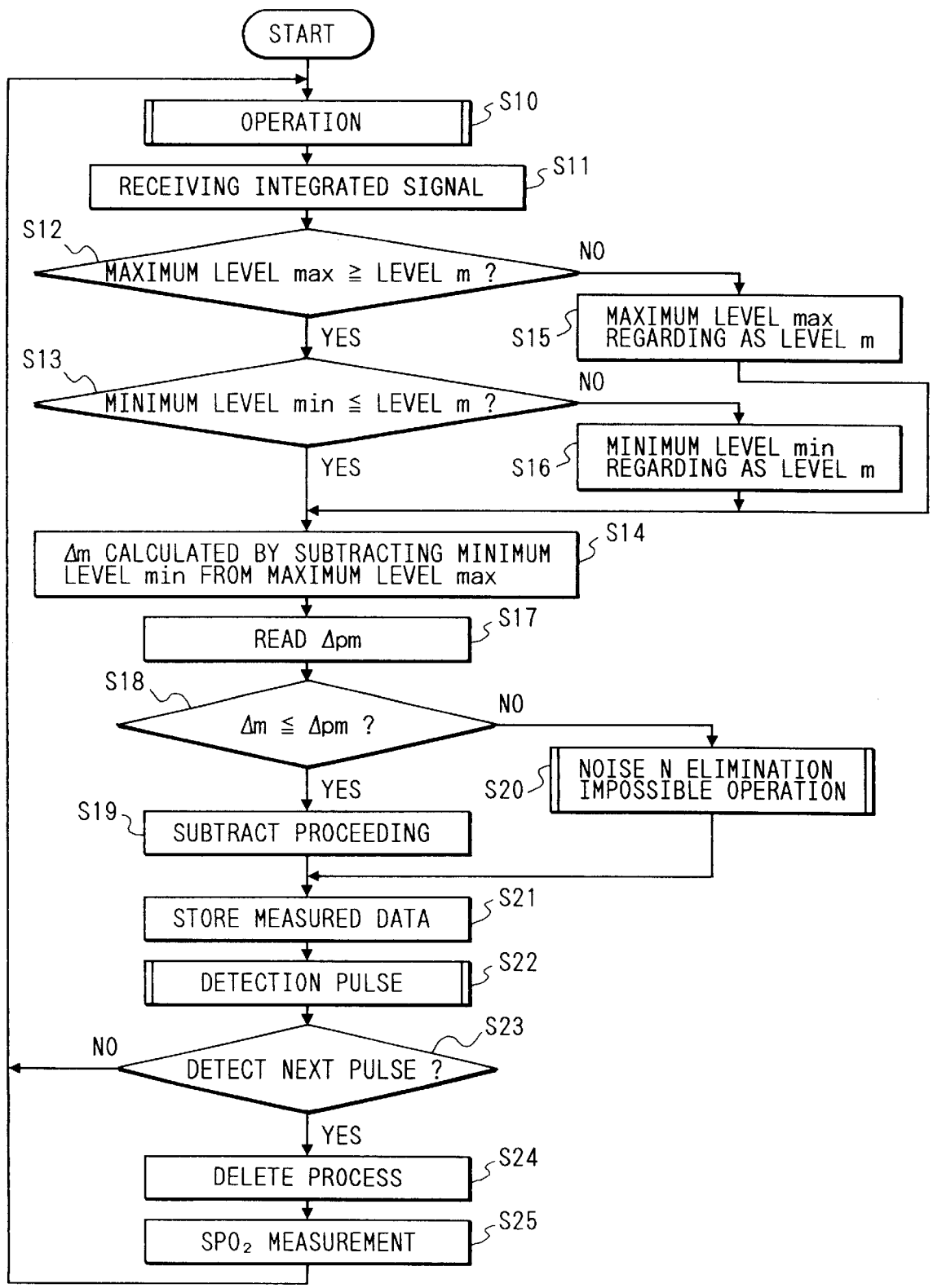
FIG. 4 is a flowchart showing a processing procedure in the case where noise is present in the first embodiment.

FIGS. 3(a) to (g) are timing charts showing the waveforms of signals processed at respective circuits and the processing timings when noise close to the frequency f is present; and FIG. 4 is a flowchart showing a processing procedure when noise close to the frequency f is present. Referring to FIGS. 1 to 4, in Step 10 in FIG. 4, the pulse oximeter operates in a manner similar to FIGS. 2(a) to (g) and outputs the integrated signal Sr to the control circuit 13 from the integrator 22 through the A/D converter 23, the integrated signal Sr having the R signal Sra, the IR signal Srb, and the dark signal Src in succession.

Then, a routine for checking a dark signal Src level change within a single stroke of the pulse of a subject shown in FIGS. 3(c), (d), (g) is executed. Here, as shown in FIG. 3 (c) and (d), a noise signal is superimposed on the amplified light-receiving signal Sd and the detection signal Se. The R signal Sra, the IR signal Srb, the dark signal Src in an integrated signal Sr, obtained by causing the detection signal Se having the noise superimposed thereon to be integrated by the integrator 22, exhibit levels with the noise superimposed thereon, respectively, as shown in FIG. 3(g). In Step 11, the control circuit 13 causes the CPU 13a thereof to receive such integrated signal Sr.

Then, in Step 12, a level m of the current dark signal Src and a maximum level max of the dark signals Src up to the last dark signal stored in the RAM 13c are read and compared, and if the level m of the current dark signal Src is smaller than the maximum level max of the dark signals Src up to the last dark signal (Yes), then a next Step 13 will be executed. In Step 13, the level m of the current dark signal Src and a minimum level min of the dark signals Src up to the last dark signal stored in the RAM 13c are read and compared, and if the level m of the current dark signal Src is larger than the minimum level min of the dark signals Src up to the last dark signal (Yes), then Step 14 will be executed.

On the other hand, if the level m of the current dark signal Src is larger than the maximum level max of the dark signals Src up to the last dark signal (No), then a next Step 15 will be executed so that the current level is regarded as the maximum level max, and Step 14 will thereafter be executed. Further, if the level m of the current dark signal Src is smaller than the minimum level min of the dark signals Src up to the last dark signal (No), then Step 16 will be executed so that the current level is regarded as the minimum level min, and Step 14 will thereafter be executed.

In Step 14, a level change Δm of a dark signal Src in the single stroke of the pulse of the subject is calculated by subtracting the minimum level min from the maximum level max determined in Steps 12, 13, 15, 16 to determine the maximum and minimum levels of the dark signal Src. Then, in Step 17, a level change allowance Δpm stored in the RAM 13c or the like in advance is read. In Step 18, whether the level change Δm calculated in Step 14 is within the level change allowance Δpm read in Step 17 or not is judged. That is, whether the level m of the dark signal Src is approximate or not is judged in this way. In this case, as shown in FIG. 3(g), the R signal Sra becomes such as indicated by the solid line obtained by adding a noise N1 level to an R signal component indicated by the one dot chain line; the IR signal Srb becomes such as indicated by the solid line obtained by adding a noise N2 level to an IR signal component indicated by the one dot chain line; and the dark signal Src consists only of a noise N level.

If the level m of the noise N that is an integrated value in the dark interval from the integrator 22 is judged to be approximate in Step 18, then the CPU 13a within the control circuit 13 subtracts the noise N level, i.e., the noise N1 level from the R signal Sra, which is a signal obtained by adding the noise N1 level to the R signal component in the integrated signal Sr shown in FIG. 3(g) which has been read by the CPU 13a. Further, the CPU 13a similarly subtracts the noise N level, i.e., the noise N2 level from the IR signal Srb obtained by adding the Noise N2 level to the IR signal component. Accordingly, an R signal Sra consisting only of the R signal component and an IR signal Srb consisting only of the IR signal component can be extracted.

If the level change Δm is judged to be larger than the level change allowance Δpm in Step 18 (No), then, as will be described in FIG. 5, the noise N in the dark interval is discrete and the level change Δm is not approximate. Therefore, the noise cannot be eliminated. Hence, a subroutine in Step 20 is executed to warn the operator that there is a noise affecting accurate measurement, and Step 21 will thereafter be executed.

Then, if measurement for a single pulse stroke is completed by the routines up to Step 20, then in Step 21, the measured data is stored in the RAM 13c within the control circuit 13 shown in FIG. 1. Then, in order to judge the end of the single pulse stroke, a next pulse is detected in Step 22; the detection is judged in Step 23. If the detection of the next pulse cannot be judged (No), then the current measurement is continued in Step 10. If, on the other hand, the detection of the next pulse is judged in Step 23 (Yes), the maximum level max and minimum level min data determined at the last measurement and stored at a predetermined working address (area) in the RAM 13c is deleted.

The $SPO_2$ is thereafter calculated and transmitted from the radio transmission section 20. Then, the measurement of $SPO_2$ in a next pulse stroke is started again in Step 10.

As described above, the first embodiment is provided as: dividing a data sampling time (cycle T) into three intervals to arrange the first R light emission interval, the second IR light emission interval, and the dark, no emission interval; causing the CPU 13a to receive the noise N level at the time of no light emission for a plurality of data sampling times (cycle T); subtracting the noise N level from the R signal Sra level and the IR signal Srb level to obtain only the R signal component level and the IR signal component level corresponding to the transmitted light level or reflected light level. Therefore, it is these R signal component level and IR signal component level that contribute to accurate $SPO_2$ measurement.

Figure 5:
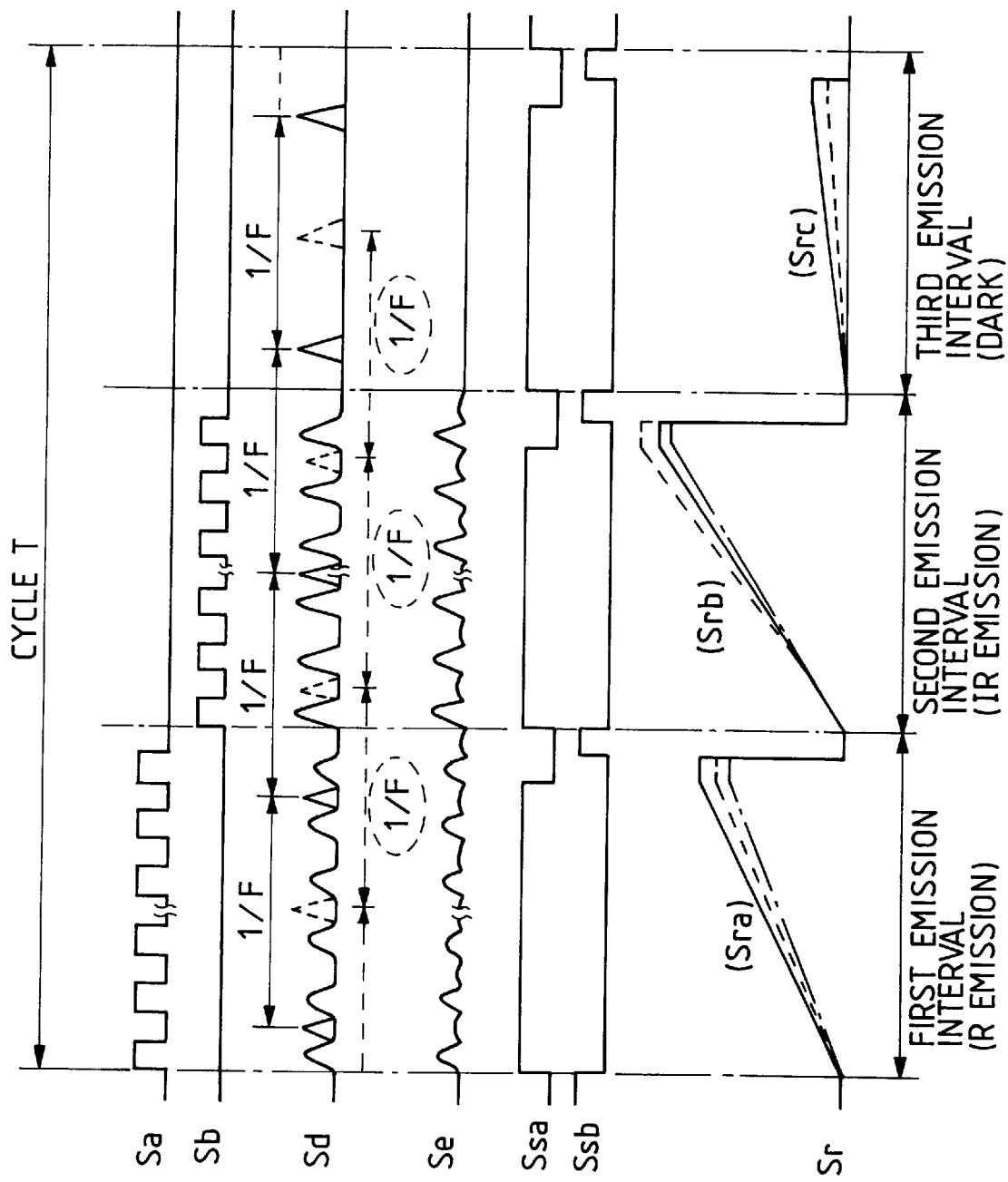
FIGS. 5(a) to (g) are timing charts showing the waveforms of processed signals and the processing timings in an operation of a second embodiment of the invention.
Figure 6:
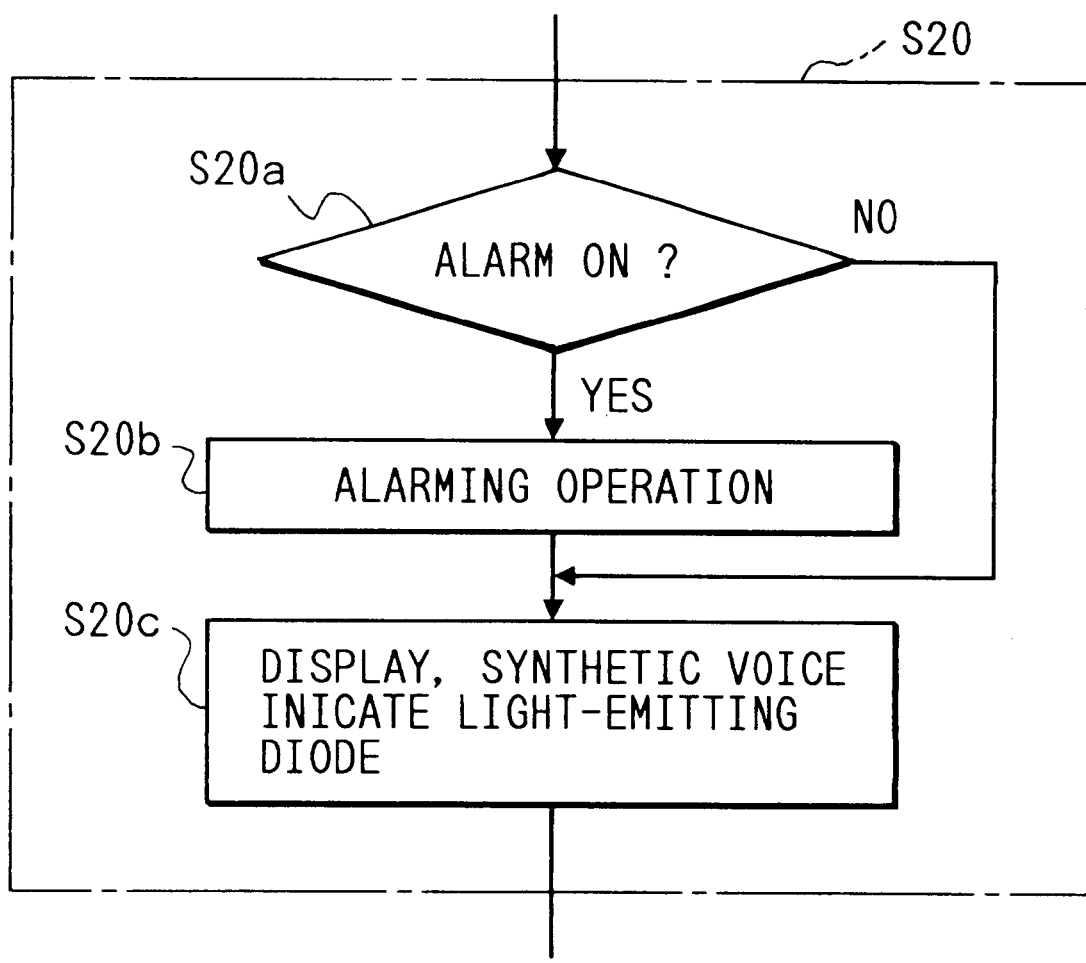
FIG. 6 is a flowchart showing a processing procedure in the operation of the second embodiment.

FIG. 5 is a timing chart showing the waveforms of processed signals and the processing timings in an operation of a second embodiment; and FIG. 6 is a flowchart showing the subroutine in Step 20. In FIGS. 1, 2, 5, 6, the subroutine in step 20 is to alarm the operator by giving an indication that accurate measurement cannot be made for the reasons that the noise N in the dark interval is discrete, that the level change Δm is not approximate, and therefore that the noise cannot be eliminated when the level change Δm is judged to be larger than the level change allowance Δpm in Step 18 (No).

The R and IR light emission drive signals Sa, Sb shown in FIGS. 5(a), (b) cause the light-emitting diodes to emit R light and IR light in the first interval and the subsequent second interval, respectively, in the configuration shown in FIG. 1, each of the first and second intervals having a cycle of T/3. When the light-receiving signal corresponding to these light emissions from the light-receiving diode 14 is converted to a voltage by the current/voltage converting and amplifying circuit 15 and is further amplified, the amplified light-receiving signal Sd shown in FIG. 5(c) may, in some cases, contain a repetitive noise whose frequency is F, which is different from the light-emitting frequency f.

In this case, a beat signal (a triangular waveform in FIG. 5(c)) indicated by the solid line and the broken line (a next repetition) in the amplified light-receiving signal Sd of FIG. 5(c) is generated in the amplified light-receiving signal Sd due to a phase difference between the cycle T/3 and the frequency F, the cycle T/3 being the cycle of the R light emission in the first interval, the IR light emission in the second interval, or no light emission in the third interval into which intervals a data sampling time (cycle T) is divided.

Therefore, as a result of the beat signal, the R signal Sra in the integrated signal Sr shown in FIG. 5(g) within each data sampling time (cycle T) changes the level thereof every cycle of the beat signal such as a signal indicated by the broken line or the solid line obtained by adding the beat signal indicated by the solid line and the broken line (the next repetition) to the R signal component derived only from the R light emission indicated by the one dot chain line. The IR signal Srb changes the level thereof every cycle of the beat signal such as a signal indicated by the broken line or the solid line obtained by adding the beat signal indicated by the solid line and the broken line (the next repetition) to the IR signal component derived only from the R light emission indicated by the one dot chain line. The dark signal Src also similarly changes the level thereof every cycle of the beat signal as indicated by the solid line or the broken line.

Thus, the levels of the R signal Sra, the IR signal Srb, the dark signal Src in the integrated signal Sr are changed by the beat signal in the time domain. The integrated value of the dark signal Src also changes the level thereof every sampling if beat is generated. Therefore, even if the noise N level has been subtracted, the R signal component level and the IR signal component level derived only from the R light emission and only from the IR light emission of cannot be obtained. In this case, a large change in the beat signal level in the time domain prevents accurate $SPO_2$ measurements from being made.

At this instance, if it is judged by the CPU 13a that the level change Δm is larger than the level change allowance Δpm in Step 18 (No), i.e., that a change in the noise component N caused by a beat signal is so large as to affect allowable $SPO_2$ measurements as a result of the observation of a time-dependent change in the level of only the noise component N in the dark signal Src, then such condition is displayed on the display section 24 not only through the control of the CPU 13a but also through the processing of the external I/O control section 13d. First, in Step 20a in FIG. 6, it is judged whether the output of an alarm by means of the loudspeaker 26 is set to the RAM 13c through the operation switch section 25 via the external I/O control section 13d and the CPU 13a is judged. If it is judged that the output of an alarm is set in Step 20a (Yes), then the alarming operation by means of the loudspeaker 26 is performed by the CPU 13a in Step 20b.

If, on the other hand, the output of an alarm is not set in Step 20a (No), then Step 20c will be executed. In Step 20c, the operation of displaying a message that the noise affects accurate measurement on the display section 24 through characters and symbols is performed by the control of the CPU 13a. In addition to the alarming by means of the loudspeaker 26 and the displaying of characters and symbols on the display section 24, an alarm is output from the loudspeaker 26 in the form of a synthetic voice by controlling the synthetic voice circuit 27 shown in FIG. 1. Further, to facilitate visual recognition, the alarm is indicated by blinking the light-emitting diode 28.

As described above, the second embodiment is provided as displaying the message that an externally derived noise level cannot be eliminated by means of an on-screen display, a sound output, a synthetic voice output, and a blinking when it is judged that noise signal levels in a plurality of data sampling cycles among the data stored in the RAM 13c are not approximate. Therefore, when the noise affects accurate measurement, the operator can be informed of such situation with ease. As a result, the operator can take such measures to eliminate noise-induced disturbance as changing the site of measurement and turning off fluorescent lamps and the like, so that accurate measurement can be made thereafter.

Figure 7:
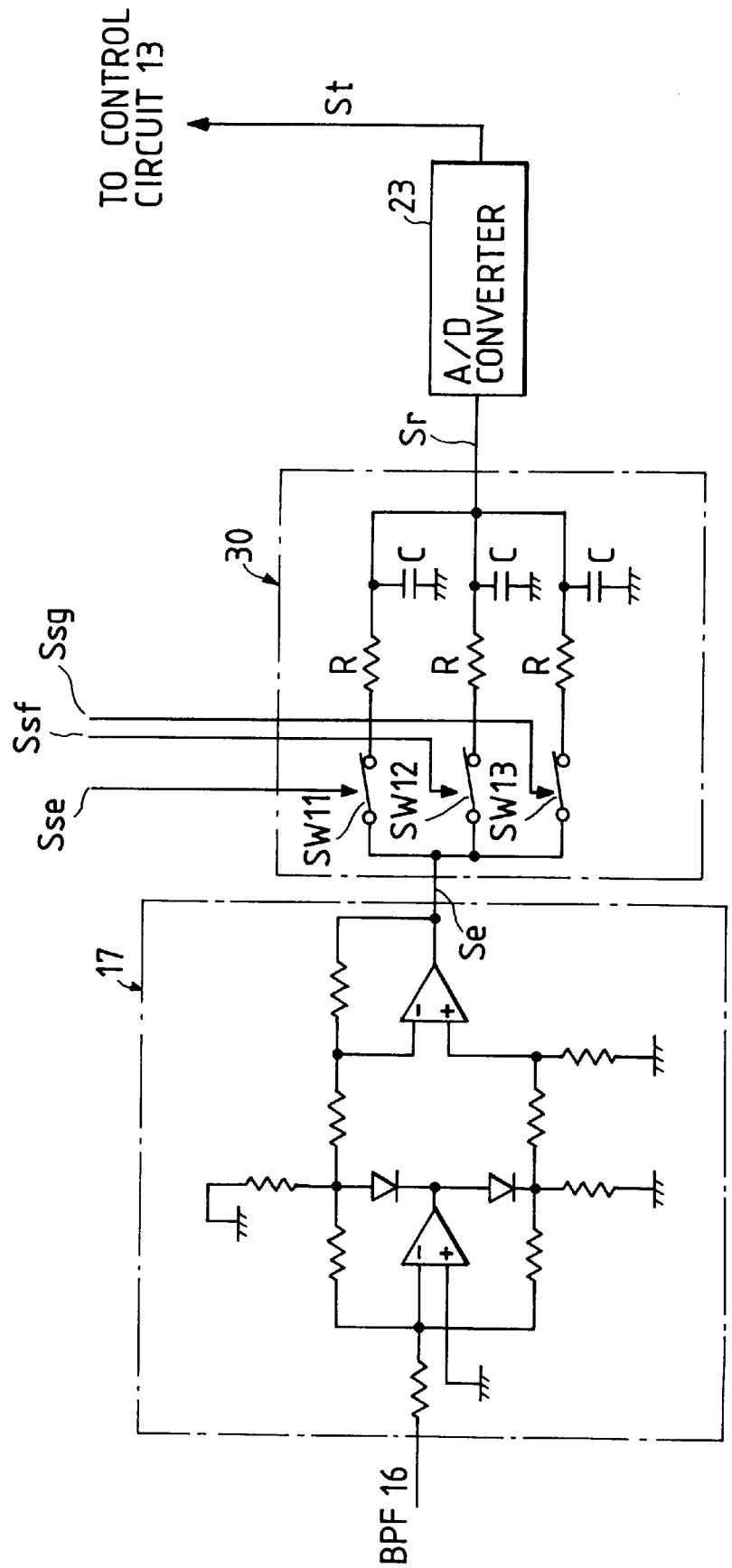
FIG. 7 is a block diagram showing a configuration of a third embodiment of the invention with part of circuits thereof.
Figure 8:
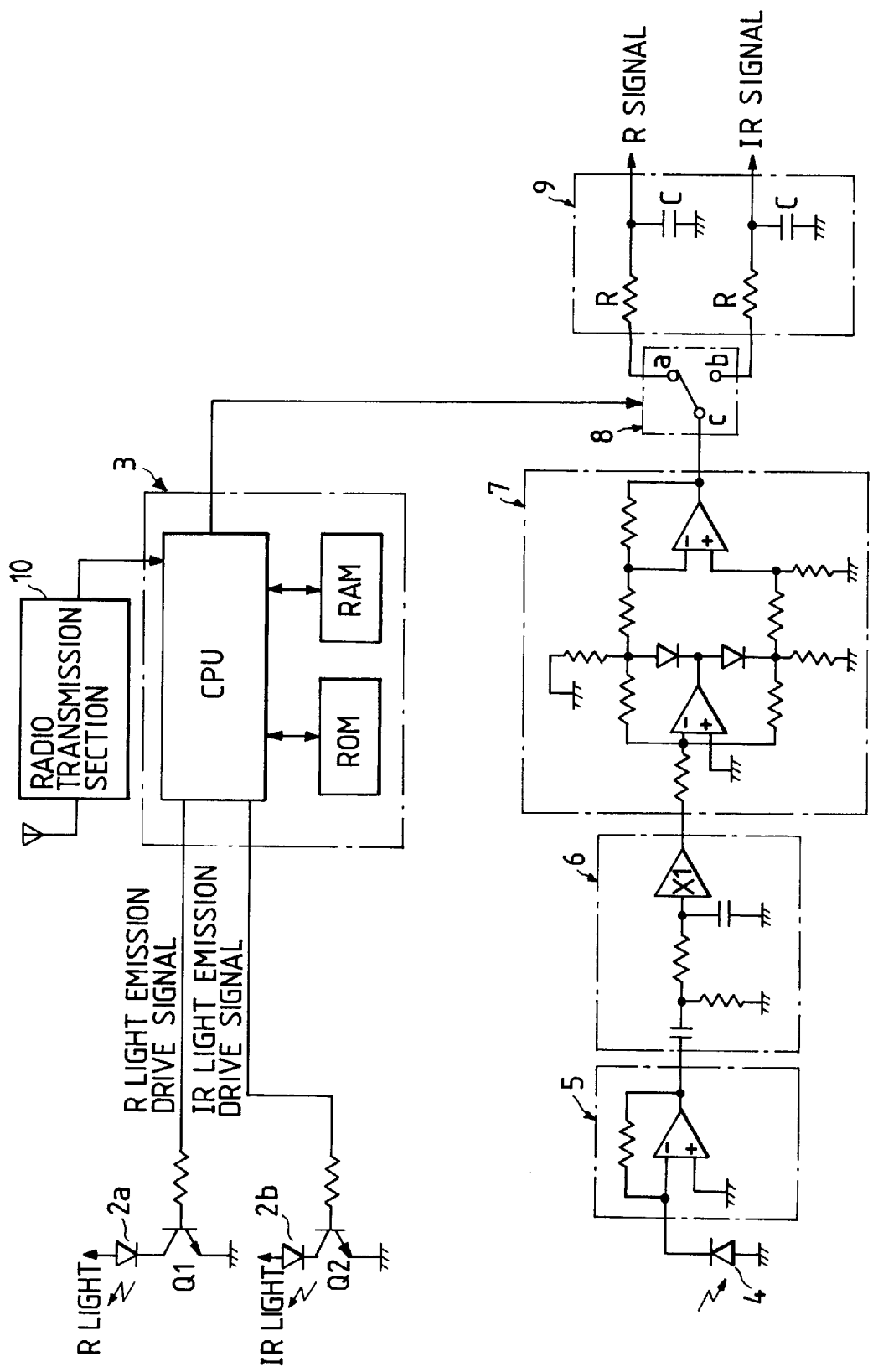
FIG. 8 is a block diagram showing a configuration of a conventional pulse oximeter with part of circuits thereof.

FIG. 7 is a block diagram showing a configuration of a third embodiment of the invention with part of circuits thereof. The third embodiment is provided as using a sample hold circuit 30 having a high frequency cutoff characteristic instead of the integrator 22 shown in FIG. 1. The sample hold circuit 30 has switches SW11, SW12, SW13, resistors R, and capacitors C. The switches SW11, SW12, SW13 are sequentially turned on and off by control signals Sse, Ssf, Ssg corresponding to R light emission in a first interval, IR light emission in a second interval, and no light emission in a third interval, into which intervals a cycle T is divided. The resistors R and the capacitors C are provided to integrate outputs of the switches SW11 to SW13, respectively. Other configurational aspects are the same as those of the first embodiment shown in FIG. 1.

In this configuration, the switches SW11 to SW13 of the sample hold circuit 30 are turned on upon rise of the R light emission in the first interval, the IR light emission in the second interval, and no light emission in the third interval into which intervals the cycle T is divided and turned off upon fall thereof to output an integrated signal Sr (an R signal Sra, an IR signal Srb, and a dark signal Src). Other operations are the same as those of the first embodiment shown in FIGS. 1 to 5, and the advantages thereof are also similar to those of the first embodiment.

In the first and second embodiments, the effect of the dark interval by the offset of the amplifiers used in the AM detecting circuit 17 and the integrator 22 on the downstream side of the BPF 16 can be eliminated simultaneously. Therefore, there is an advantage that offset adjustment is dispensed with.

As is apparent from the foregoing, the pulse oximeter of the present invention detects a noise signal level at the no light emission interval from a light-receiving signal of the transmitted light or reflected light obtained when light emission in the red light emission interval, the infrared light emission interval, and the no light emission interval is repeated with respect to the object to be measured every data sampling cycle, and obtains only a light-receiving signal level corresponding to the transmitted light or reflected light obtained by subtracting the noise signal level from the light-receiving signal level. Therefore, accurate measurements with such an external noise level as affecting quantitatively detected $SPO_2$ measurement eliminated can be obtained.

The pulse oximeter stores light-receiving signal levels corresponding to the red light emission, infrared light emission, and no light emission intervals as well as noise signal levels corresponding to the no light emission interval in a plurality of data sampling cycles, and outputs a signal level obtained by subtracting the noise signal level from each of light-receiving signal levels at the time of the red light emission and the infrared light emission when the noise signal levels in the stored data in the plurality of data sampling cycles are approximate. Therefore, accurate measurements with such an external noise level as affecting quantitatively detected $SPO_2$ measurement eliminated can be obtained.

The pulse oximeter given an indication that an external noise level cannot be eliminated by means of an on-screen display, a sound output, a synthetic voice output, a light emission either singly or in combination when the judging means judges that the noise signal levels in the plurality of data sampling cycles among the data stored in the storage means are not approximate. Therefore, if the external noise affects accurate measurement, the pulse oximeter alarms the operator by displaying such condition. As a result of this operation, the operator can take such effective measures as stopping the measurement at a site full of disturbance and turning off the power sources of noise generating devices at another site or at the same site so that accurate measurement can be made thereafter.

What is claimed is:

1. A pulse oximeter comprising:

light-emitting means for repeating, successively, red light emission, infrared light emission, and no light emission, with respect to an object to be measured, in every data sampling cycle in measurement of a saturated oxygen in arterial blood;

light-receiving means for outputting a light-receiving signal obtained by receiving transmitted light and reflected light reflected from the object to be measured;

noise level detecting means for detecting, from the light-receiving signal, a noise signal level at the time of no light emission; and signal generating means for processing the light-receiving signal to obtain a measurement signal having a level corresponding only to the red light emission and the infrared light emission by subtracting the noise signal level from the light-receiving signal.

2. The pulse oximeter as claimed in claim 1, further comprising:

storage means for storing, in each of a plurality of data sampling cycles repeated by the light-emitting means, the light-receiving signal corresponding to the red light emission, the infrared light emission, and the no light emission as well as the noise signal level corresponding to the no light emission; and judging means for judging whether the noise signal level in each of the plurality of data sampling cycles is within a predetermined range, wherein when the judging means judges that the noise signal level is within the predetermined range, the signal generating means outputs a the measurement signal having a level corresponding only to the red light emission and the infrared light emission obtained by subtracting the noise signal level from the light-receiving signal.

3. The pulse oximeter as claimed in claim 2, wherein the light-receiving means includes an integrating circuit for generating an integrated light-receiving signal by integrating the light-receiving signal from a light-receiving element included in the light-receiving means; wherein a level of the integrated light-receiving signal is stored in the storage means as the light-receiving signal.

4. The pulse oximeter according to claim 2, further comprising:

alarm means for outputting an alarm to inform a user that an external noise level cannot be eliminated, said alarm comprising an on-screen display, a sound output, a synthetic voice output, and a light emission said alarm being output when the judging means judges that the noise signal level in the plurality of data sampling cycles is not within the predetermined range.

5. The pulse oximeter according to claim 4, wherein the alarm means outputs one of the on-screen display, the sound output, the synthetic voice output, and the light emission.

6. The pulse oximeter as claimed in claim 1, wherein the light-receiving means includes an integrating circuit for generating an integrated light-receiving signal by integrating the light-receiving signal from a light-receiving element included in the light-receiving means; wherein a level of the integrated light-receiving signal is stored in a storage means as the light-receiving signal.

7. A method for measuring a saturated oxygen in arterial blood, comprising the steps of:

repeating, successively, red light emission, infrared light emission, and no light emission, with respect to an object to be measured, in every data sampling cycle in measurement of the saturated oxygen in the arterial blood;

outputting a light-receiving signal obtained by receiving transmitted light and reflected light reflected from the object to be measured;

detecting, from the light-receiving signal, a noise signal level at the time of no light emission; and obtaining a measurement signal having a level corresponding only to the red light emission and the infrared light emission by subtracting the noise signal level from the light-receiving signal.

8. The method for measuring a saturated oxygen in arterial blood as claimed in claim 7, further comprising the steps of:

storing, in each of a plurality of data sampling cycles, the light-receiving signal corresponding to the red light emission, the infrared light emission, and the no light emission as well as the noise signal level corresponding to the no light emission;

judging whether the noise signal level in each of the plurality of data sampling cycles is within a predetermined range; and outputting the measurement signal having a level corresponding only to the red light emission and the infrared light emission obtained by subtracting the noise signal level from each of the light-receiving signal when the noise signal level is within the predetermined range.

9. The method for measuring a saturated oxygen in arterial blood as claimed in claim 8, further comprising:

informing a user that an external noise level cannot be eliminated by displaying a message on an on-screen display, outputting a sound, outputting a synthetic voice sound, and emitting a light when the noise signal level in each of the plurality of data sampling cycles is not within the predetermined range.

10. The method for measuring a saturated oxygen in arterial blood as claimed in claim 9, wherein the informing step comprises the step of performing one of displaying the message on the on-screen display, outputting the sound, outputting the synthetic voice sound, and emitting the light.

11. An apparatus for measuring light-absorbing material in blood comprising:

light-emitting means for repeating red light emission, infrared light emission, and no light emission, with respect to an object to be measured, successively in every data sampling cycle in measurement of a light-absorbing material in blood;

light-receiving means for outputting a light-receiving signal obtained by receiving transmitted light or reflected light reflected from the object to be measured;

noise level detecting means for detecting, from the light-receiving signal, a noise signal level at the time of no light emission;

signal generating means for processing the light-receiving signal to obtain a measurement signal having a level corresponding to the red light emission and the infrared light emission by subtracting the noise signal level from the light-receiving signal;

storage means for storing, in each of a plurality of data sampling cycles repeated by the light-emitting means, the light-receiving signal corresponding to the red light emission, the infrared light emission, and the no light emission as well as the noise signal level corresponding to the no light emission;

wherein the light-receiving means includes an integrating circuit for generating an integrated light-receiving signal by integrating the light-receiving signal from a light-receiving element included in the light-receiving means; and control means for starting integration and discharging said integrated light-receiving signal at said integrated circuit in synchronism with said data sampling cycles; and judging means for judging whether the noise signal level in each of the plurality of data sampling cycles is within a predetermined range, wherein when the judging means judges that the noise signal level is within the predetermined range, the signal generating means outputs the measurement signal having a level corresponding to the red light emission and the infrared light emission obtained by subtracting the noise signal level from the light-receiving signal.

12. An apparatus for measuring light-absorbing material in blood comprising:

light-emitting means for repeating red light emission, infrared light emission, and no light emission, with respect to an object to be measured, successively in every data sampling cycle in measurement of a light-absorbing material in blood;

light-receiving means for outputting a light-receiving signal obtained by receiving transmitted light or reflected light reflected from the object to be measured;

noise level detecting means for detecting, from the light-receiving signal, a noise signal level at the time of no light emission;

signal generating means for processing the light-receiving signal to obtain a measurement signal having a level corresponding only to the red light emission and the infrared light emission by subtracting the noise signal level from the light-receiving signal;

storage means for storing, in each of a plurality of data sampling cycles repeated by the light-emitting means, the light-receiving signal corresponding to the red light emission, the infrared light emission, and the no light emission as well as the noise signal level corresponding to the no light emission;

wherein the light-receiving means includes an integrating circuit for generating an integrated light-receiving signal by integrating the light-receiving signal from a light-receiving element included in the light-receiving means; and judging means for judging whether the noise signal level in each of the plurality of data sampling cycles is within a predetermined range, wherein said judging means judges whether the noise level is within said predetermined range based on a comparison of a portion of said integrated light-receiving signal, corresponding to the no light emission, stored in the storage means with one of a maximum and minimum level a portion of previous integrated light-receiving signals corresponding to no light emission; and wherein when the judging means judges that the noise signal level is within the predetermined range, the signal generating means outputs the measurement signal having a level corresponding to the red light emission and the infrared light emission obtained by subtracting the noise signal level from the light-receiving signal.

13. The apparatus for measuring light-absorbing material in blood, as claimed in claim 12, further comprising:

alarm means for outputting an alarm to inform a user that an external noise level cannot be eliminated, said alarm being output when the judging means judges that the noise signal level in the plurality of data sampling cycles is not within the predetermined range.

14. The apparatus for measuring light-absorbing material in blood, as claimed in claim 12, further comprising:

control means for clearing said integrated light-receiving signal stored in said storage means at predetermined intervals.

15. An apparatus for measuring light-absorbing material in blood comprising:

light-emitting means for repeating red light emission, infrared light emission, and no light emission, with respect to an object to be measured, successively in every data sampling cycle in measurement of a light-absorbing material in blood;

light-receiving means for outputting a light-receiving signal obtained by receiving transmitted light or reflected light reflected from the object to be measured;

noise level detecting means for detecting, from the light-receiving signal, a noise signal level at the time of no light emission;

signal generating means for processing the light-receiving signal to obtain a measurement signal having a level corresponding to the red light emission and the infrared light emission by subtracting the noise signal level from the light-receiving signal;

storage means for storing, in each of a plurality of data sampling cycles repeated by the light-emitting means, the light-receiving signal corresponding to the red light emission, the infrared light emission, and the no light emission as well as the noise signal level corresponding to the no light emission;

wherein the light-receiving means includes an integrating circuit for generating an integrated light-receiving signal by integrating the light-receiving signal from a light-receiving element included in the light-receiving means; and judging means for judging whether the noise signal level in each of the plurality of data sampling cycles is within a predetermined range, wherein said judging means judges whether the noise signal level is within said predetermined range based on a comparison of a value obtained by subtracting a minimum level of portion of said integrated light-receiving signal corresponding to no light emission from a maximum level of a corresponding portion of a previous integrated light-receiving signal stored in said storage means, with a predetermined threshold level; and wherein when the judging means judges that the noise signal level is within the predetermined range, the signal generating means outputs the measurement signal having a level corresponding to the red light emission and the infrared light emission obtained by subtracting the noise signal level from the light-receiving signal.

16. The apparatus for measuring light-absorbing material in blood, as claimed in claim 15, further comprising:

alarm means for outputting an alarm to inform a user that an external noise level cannot be eliminated, said alarm being output when said judging means judges that the noise signal level in said plurality of data sampling cycles is not within the predetermined range.

17. The apparatus for measuring light-absorbing material in blood, as claimed in claim 15, further comprising:

control means for clearing said integrated light-receiving signal from said storage means at predetermined intervals.

18. A method for measuring light-absorbing material in blood, comprising the steps of:

repeating red light emission, infrared light emission, and no light emission, with respect to an object to be measured, successively in every data sampling cycle in measurement of the light-absorbing material in blood;

outputting a light-receiving signal obtained by receiving transmitted light and reflected light reflected from the object to be measured;

detecting, from said light-receiving signal, a noise signal level at the time of no light emission;

obtaining a measurement signal having a level corresponding to the red light emission and the infrared light emission by subtracting the noise signal level from said light-receiving signal;

storing, in each of a plurality of data sampling cycles, said light-receiving signal corresponding to the red light emission, the infrared light emission, and the no light emission as well as the noise signal level corresponding to the no light emission;

judging whether the noise signal level in each of the plurality of data sampling cycles is within a predetermined range, by comparing a portion of a current integrated light-receiving signal corresponding to no light emission with one of a maximum and a minimum level of portions of previous integrated light-receiving signals corresponding to no light emission; and outputting the measurement signal having a level corresponding to the red light emission and the infrared light emission obtained by subtracting the noise signal level from each of the light-receiving signals when the noise signal level is within the predetermined range.

19. The method as claimed in claim 18, further comprising the steps of:

informing a user that an external noise level cannot be eliminated when the noise signal level in each of the plurality of data sampling cycles is not within the predetermined range.

20. The method as claimed in claim 18, further comprising the steps of:

clearing said integrated light-receiving signal and repeating the previous steps at predetermined intervals.

21. A method for measuring light-absorbing material in blood, comprising the steps of:

repeating red light emission, infrared light emission, and no light emission, with respect to an object to be measured, successively in every data sampling cycle in measurement of the light-absorbing material in blood;

outputting a light-receiving signal obtained by receiving transmitted light and reflected light reflected from the object to be measured;

detecting, from the light-receiving signal, a noise signal level at the time of no light emission;

obtaining a measurement signal having a level corresponding to the red light emission and the infrared light emission by subtracting the noise signal level from the light-receiving signal;

storing, in each of a plurality of data sampling cycles, the light-receiving signal corresponding to the red light emission, the infrared light emission, and the no light emission as well as the noise signal level corresponding to the no light emission;

judging whether the noise signal level is within a range from a minimum level to a maximum level of a previous noise signal;

subtracting a minimum value of a portion of said integrated light-receiving signal corresponding to the no light emission from a maximum value of said portion of said integrated light-receiving signal corresponding to the no light emission to obtain a subtraction value;

comparing said subtraction value with a predetermined threshold level when said integrated light-receiving signal is not within said range; and outputting the measurement signal having a level corresponding to the red light emission and the infrared light emission obtained by subtracting the noise signal level from each of the light-receiving signals corresponding to the red light emission and the infrared light emission when the noise signal level is within the range.

22. The method as claimed in claim 21, further comprising the steps of:

informing a user that an external noise level cannot be eliminated when the noise signal level in each of the plurality of data sampling cycles is not within the predetermined range.

23. The method as claimed in claim 21, further comprising the step of:

clearing said integrated light-receiving signal and repeating the previous steps at predetermined intervals.

* * * * *